United States Patent
Borsotti et al.

(10) Patent No.: US 6,492,569 B1
(45) Date of Patent: Dec. 10, 2002

(54) PROCESS FOR THE PREPARATION OF TETRAFLUOROHALOGENBENZENES

(75) Inventors: Giampietro Borsotti, Novara; Anna Sommazzi, Santa Margherita Ligure; Roberto Santi, Novara, all of (IT)

(73) Assignee: Enichem S.p.A., Milan (IT)

( * ) Notice: Subject to any disclaimer, the term of this patent is extended or adjusted under 35 U.S.C. 154(b) by 0 days.

(21) Appl. No.: 09/926,754

(22) PCT Filed: Jun. 2, 2000

(86) PCT No.: PCT/EP00/05097

§ 371 (c)(1),
(2), (4) Date: Dec. 12, 2001

(87) PCT Pub. No.: WO00/76946

PCT Pub. Date: Dec. 21, 2000

(30) Foreign Application Priority Data

Jun. 15, 1999 (IT) .......................................... MI99A1329

(51) Int. Cl.⁷ ............................................... C07C 22/00
(52) U.S. Cl. ...................................................... 570/147
(58) Field of Search .......................................... 570/147

(56) References Cited

U.S. PATENT DOCUMENTS

| | | | |
|---|---|---|---|
| 3,424,804 A | | 1/1969 | Tilney-Bassett |
| 5,847,241 A | * | 12/1998 | Oren |
| 6,307,113 B1 | * | 10/2001 | Sabahi |

OTHER PUBLICATIONS

J. Burdon et al.: "Aromatic polyfluoro compounds—XXXIV Nucleophilic replacement reactions of some tetrafluorohalogenbenzenes"vol. 22, 1966, pp. 2541–2549 cited in the application p. 2545.

* cited by examiner

*Primary Examiner*—Alan Siegel
(74) *Attorney, Agent, or Firm*—Oblon, Spivak, McClelland, Maier & Neustadt, P.C.

(57) ABSTRACT

A process is described for the preparation of compounds having the formula (I) $C_6F_4HX$, wherein X is Br or Cl, which comprises reacting tetrafluorobenzene with a halogen in the presence of a Lewis acid catalyst.

10 Claims, No Drawings

PROCESS FOR THE PREPARATION OF TETRAFLUOROHALOGENBENZENES

This application is a 371 of PCT/EP00/05097 filed Jun. 2, 2000.

The present invention relates to a process for the preparation of compounds having the formula (I) $C_6F_4HX$ wherein X is Br or Cl.

More specifically, the present invention relates to a method for the preparation of 1-bromo-2,3,4,5-tetrafluorobenzene.

The compounds having the formula (I) are useful intermediates for the synthesis, for example, of fluorinated fluorenes which are used as polymerization cocatalysts of α-olefins.

The preparation of compounds having the formula (I) by reacting the halogen with tetrafluorobenzene in oleum ($SO_3$ in sulfuric acid), is known in the art.

For example the patent U.S. Pat. No. 3,424,804 describes a synthesis method which comprises (i) a first step in which tetrafluorobenzene is reacted with bromine in oleum, to produce a mixture containing monobromo- and dibromotetrafluorobenzene, and (ii) a second step in which the dibromotetrafluorobenzene coming from the first step is reduced with zinc powder, in glacial acetic acid, to give the compound monobromotetrafluorobenzene.

Operating according to this process a final yield of the compound monobromotetrafluorobenzene of 58% is obtained.

Bourdon et al. (Tetrahedron, 22, 2541–2549, 1966) describe a method for the preparation of tetrafluorobromobenzene which consists in reacting tetrafluorobenzene with bromine at 0° C., in oleum at 20% in the presence of $AlBr_3$ 1%.

The halogenation reaction is a typical substitution reaction at the aromatic ring and is characterized by the co-presence of secondary reactions, parallel and subsequent to the main reaction (monohalogenation). The most important of these secondary reactions are the subsequent halogenations of the monohalogenation product, with the formation of dihalogenated products.

In the case of the bromination of tetrafluorobenzene with bromine therefore, more or less significant quantities of dibromotetrafluorobenzene are formed, together with the main product.

Other by-products, such as sulfuric derivatives of tetrafluorobenzene soluble in water, cannot on the other hand be recovered and their formation must be limited to reduce specific consumptions of this compound, which is extremely costly, and raise the process yield.

These known processes therefore substantially present the drawbacks deriving from problems relating to corrosion and low yields and selectivity of the product in question.

The objective of the present invention is to obtain compounds having the formula (I) with high yields and selectivities, by means of a process which is simple, economic and easy to effect on an industrial scale and which does not have the disadvantages of the processes of the known art.

It has now been found that this target can be reached if the reaction between tetrafluorobenzene and halogen is carried out in the presence of a Lewis acid catalyst and in the absence of a solvent of the oleum type.

The process of the present invention allows the useful reaction product to be obtained with high yields and selectivities.

In accordance with this, the present invention relates to a method for the preparation of compounds having the formula (I) $C_6F_4HX$ wherein X is Br or Cl, which comprises:

(a) reacting tetrafluorobenzene with the halogen with a ratio ranging from 0.5 to 1 mole per mole of tetrafluorobenzene, in the presence of a Lewis acid catalyst, and (b) recovering the compound having the formula (I) from the reaction mixture.

Catalysts suitable for the purposes of the present invention generally consist of Lewis acids such as halides of aluminum, tin, zinc, iron, titanium and zirconium. Among aluminum compounds, aluminum chloride is preferably used.

The quantity of catalyst can vary from 0.1 to 2.0% by weight, preferably from 0.5 to 1.0% by weight, per 100 g of tetrafluorobenzene.

The reaction temperatures can vary from 0 to 50° C.

The reaction time is selected in relation to the temperature; however, reaction times ranging from 0.5 to 6 hours are sufficient.

According to a preferred embodiment of the process of the present invention, the reaction between tetrafluorobenzene and the halogen is carried out in the presence of the catalyst, at 10–15° C. until hydrohalogen acid begins to develop. The temperature is then brought to values of 2 to 3° C. and, when the acid development decreases, the reaction mixture is again raised to 10–15° C.

The reaction is generally carried out at atmospheric pressure.

The process according to the present invention can be carried out batchwise, in continuous or semi-continuous.

At the end of the reaction, the compound having the formula (I) is recovered using the normal separation techniques. For example. the compound (I) can be isolated by fractionated distillation.

Operating according to the method of the present invention, high yields and selectivities of the useful reaction product can be obtained in a single step, in short times and with a low production of dihalogentetrafluorobenzene.

The following examples, whose sole purpose is to describe the present invention in greater detail, should in no way be considered as limiting the scope of the invention itself.

EXAMPLE 1

1000 g of 1,2,3,4-tetrafluorobenzene (titer 99.7%) and 400 ml of $Br_2$ are charged into a 2l glass flask, equipped with a blade stirrer, thermometer and cooler connected to an HBr absorber containing 1 liter of water.

The mixture is then brought to an internal temperature of 15° C. and 10 g of anhydrous $AlCl_3$ are added. After a few minutes the development of HBr begins and as the development rate of HBr increases, the internal temperature is lowered to a value of 1–20° C. with a cold bath.

After about 1 hour, i.e. when the development rate of HBr has visibly diminished, the solution is brought back to a temperature of 15° C. After 1.5 hours the reaction is blocked by the addition of 100 ml of water and ice.

During the test aliquots of the reaction mixture are removed, which, after treatment with sodium bisulfite at 30% to destroy the excess Br., are analyzed via gaschromaography.

The results are indicated in Table 1.

TABLE 1

| Sample | Time minutes | Tetrafluoro-benzene | 1-Bromo-2,3,4,5-tetrafluorobenzene | Dibromotetra-fluorobenzene |
|---|---|---|---|---|
| 1 | 20 | 66.3% | 33.5% | 0.2% |
| 2 | 40 | 49.6% | 49.3% | 1.1% |
| 3 | 60 | 37% | 60.5% | 2.5% |
| 4 | 90 | 25.5% | 69.2% | 5.3% |

From the data indicated in the table it can be observed that the conversion is 74.5% with a selectivity to bromotetrafluorobenzene of 92.9% and a yield of 69.2%.

At the end of the reaction 1,402 g of reaction raw product are obtained, which is anhydrified with anhydrous $Na_2CO_3$ for a night.

The raw product is then filtered in a distillation flask and rectified with an adiabatic column filled with Fenske rings having a length of 30 cm and a diameter of 26 mm. A reflux ratio of 10:1 is maintained at the head of the column. The following products are obtained:

| | |
|---|---|
| tetrafluorobenzene | 310 g |
| intermediate fraction (tetrafluorobenzene + Br tetra-fluorobenzene, 1:1) | 68 g |
| bromotetrafluorobenzene | 902 g |
| residue (monobromotetrafluorobenzene 30% and dibromo-tetrafluorobenzene 70%) | 110 g |

From these results the following yield, conversion and selectivity values can be calculated:
conversion with respect to the starting tetrafluorobenzene 65.6%
selectivity to bromotetrafluorobenzene 92.6%
yield 63.5%

EXAMPLE 2

Comparative

The same procedure is carried out as described by Bourdon et al (Tetrahedron, 22, 2541–2549, 1966)

50 g of 1,2,3,4-tetrafluorobenzene are added dropwise, over a period of 1 hour, to a stirred solution cooled to 0° C. of $Br_2$ (100 g) and $AlBr_3$ (0.5 g) in 150 ml of oleum (20% $SO_3$).

The resulting mixture is maintained for a further 5 hours at 0° C., is then hydrolyzed in ice and the excess bromine is destroyed with a solution of bisulfite.

The product is subsequently extracted with ethyl ether 25 and the extract obtained is dried on anhydrous $Na_2CO_3$, filtered and washed with ether. The ether solution is then distilled with a Vigreaux$^R$ column.

Gaschromatographic analysis (GC) of the solution gives a content of 93% of bromotetrafluorobenzene, 1% of tetrafluorobenzene and 66 of dibromotetrafluorobenzene.

After distilling the ethyl ether, a fraction (2 g) is collected at the head up to 135° C. and a fraction (25.5 g) which boils at 136–1400° C.

The GC titer with respect to bromotetrafluorobenzene is 99%.

A residue of 3.9 g consisting of bromine and dibromotetrafluorobenzene remains in the boiler in a ratio of about 1:1. The calculated yield to bromotetrafluorobenzene with respect to the distillate is 33.4%.

What is claimed is:

1. A process for the preparation of compounds having the formula (I)

$$C_6F_4HX, \qquad (I)$$

wherein

X is Br or Cl, which comprises:

(a) reacting tetrafluorobenzene and a halogen selected from the group consisting of bromine and chlorine, in a ratio of 0.5 to 1 mole per mole of tetrafluorobenzene, in the presence of a Lewis acid catalyst, and (b) recovering the compound having the formula (I) from the reaction mixture, wherein the reaction between tetrafluorobenzene and the halogen is carried out in the absence of an oleum solvent.

2. The process according to claim 1, wherein the compound having the formula (I) is 1-bromo-2,3,4,5-tetrafluorobenzene.

3. The process according to claim 1, wherein the catalyst is selected from the group consisting of halides of aluminum, halides of tin, halides of zinc, halides of iron, halides of titanium, and halides of zirconium.

4. The process according to 3, wherein the catalyst is aluminum chloride.

5. The process according to claim 1, wherein the quantity of catalyst varies from 0.1 to 2.0% by weight per 100 g of tetrafluorobenzene.

6. The process according to claim 5, wherein the quantity of catalyst varies from 0.5 to 1.0% by weight per 100 g of tetrafluorobenzene.

7. The process according to claim 1, wherein the reactor temperature ranges from 0 to 50° C.

8. The process according to claim 1, wherein the tetrafluorobenzene and the halogen are reacted for from 0.5 to 6 hours.

9. The process according to claim 1, wherein the compound having formula (I) is recovered by fractionated distillation.

10. The process according to claim 1, wherein the tetrafluorobenzene and the halogen are reacted at from 10 to 15° C. until a hydrohalogen acid develops, then the temperature is reduced to from 2 to 3° C. to decrease the development of the hydrohalogen acid, and then the temperature is raised to from 10 to 15° C.

* * * * *